(12) United States Patent
Cowley et al.

(10) Patent No.: US 8,965,499 B2
(45) Date of Patent: Feb. 24, 2015

(54) OVERWRAP FOR NERVE STIMULATION SYSTEM

(75) Inventors: Anthony W. Cowley, Houston, TX (US); Robert J Chilton, Round Rock, TX (US); Victor S. Kokx, League City, TX (US); Jeffrey H. May, Seabrook, TX (US)

(73) Assignee: Cyberonics, Inc., Houston, TX (US)

( * ) Notice: Subject to any disclaimer, the term of this patent is extended or adjusted under 35 U.S.C. 154(b) by 138 days.

(21) Appl. No.: 13/097,638

(22) Filed: Apr. 29, 2011

(65) Prior Publication Data

US 2012/0277819 A1    Nov. 1, 2012

(51) Int. Cl.
A61N 1/05    (2006.01)
A61N 1/36    (2006.01)
A61N 1/378   (2006.01)

(52) U.S. Cl.
CPC .............. *A61N 1/0558* (2013.01); *A61N 1/378* (2013.01); *A61N 1/0556* (2013.01); *A61N 1/36053* (2013.01)
USPC .......................................................... 607/2

(58) Field of Classification Search
USPC ......................................... 607/118, 148, 152
See application file for complete search history.

(56) References Cited

U.S. PATENT DOCUMENTS

| | | |
|---|---|---|
| 4,590,946 A | 5/1986 | Loeb |
| 5,324,322 A | 6/1994 | Grill, Jr. et al. |
| 5,433,996 A | 7/1995 | Kranzler et al. |
| 5,437,900 A | 8/1995 | Kuzowski |
| 5,462,781 A | 10/1995 | Zukowski |
| 5,487,756 A | 1/1996 | Kallesoe et al. |
| 5,505,201 A * | 4/1996 | Grill et al. ...................... 607/118 |
| 5,614,284 A | 3/1997 | Kranzler et al. |
| 5,833,665 A | 11/1998 | Bootman et al. |
| 5,899,933 A | 5/1999 | Bhadra et al. |
| 5,964,702 A | 10/1999 | Grill, Jr. et al. |
| 5,997,895 A | 12/1999 | Narotam et al. |
| 6,017,366 A | 1/2000 | Berman |
| 6,090,996 A | 7/2000 | Li |
| 6,596,293 B1 | 7/2003 | Bootman et al. |
| 6,600,956 B2 * | 7/2003 | Maschino et al. ............. 607/118 |
| 6,620,356 B1 | 9/2003 | Wong et al. |
| 6,652,594 B2 | 11/2003 | Francis et al. |
| 6,689,756 B2 | 2/2004 | Hesson et al. |
| 6,716,225 B2 | 4/2004 | Li et al. |
| 6,780,497 B1 | 8/2004 | Walter |
| 6,810,880 B1 | 11/2004 | Jennings, Jr. et al. |

(Continued)

FOREIGN PATENT DOCUMENTS

WO    2009135140 A1    11/2009

OTHER PUBLICATIONS

Material Properties of Silicone Rubber, Elastomers ; Polymers Data Sheets.   www.matbase.com/materials/polymers/elastomers/siliconie-rubber/properties.*

(Continued)

*Primary Examiner* — Amanda Patton
(74) *Attorney, Agent, or Firm* — Cyberonics, Inc.

(57) ABSTRACT

A nerve overwrap for an implantable nerve stimulation system includes a flexible sheet of electrically insulative material, having an electrical resistivity of from about $10^8$ ohm*m to about $10^{20}$ ohm*m, adapted to wrap substantially around a group of nerve stimulation electrodes.

24 Claims, 9 Drawing Sheets

(56) References Cited

U.S. PATENT DOCUMENTS

| | | | |
|---|---|---|---|
| 6,969,523 B1 | 11/2005 | Mattern et al. | |
| 6,991,637 B2 | 1/2006 | Crawley et al. | |
| 7,248,930 B1 | 7/2007 | Woloszko et al. | |
| 7,561,922 B2 | 7/2009 | Cohen et al. | |
| 7,596,414 B2 | 9/2009 | Whitehurst et al. | |
| 7,672,728 B2 | 3/2010 | Libbus et al. | |
| 7,805,195 B2 | 9/2010 | Zealear | |
| 7,809,442 B2 | 10/2010 | Bolea et al. | |
| 7,974,706 B2 * | 7/2011 | Moffitt et al. | 607/118 |
| 8,116,882 B2 * | 2/2012 | Kowalczewski | 607/118 |
| 2008/0027524 A1 * | 1/2008 | Maschino et al. | 607/118 |
| 2009/0210042 A1 | 8/2009 | Kowalczewski | |
| 2010/0312320 A1 | 12/2010 | Faltys et al. | |

OTHER PUBLICATIONS

International Application No. PCT/US2012/034147, International Search Report and Written Opinion dated Apr. 18, 2013, 18 pages.

International Application No. PCT/US2012/034147, International Search Report and Written Opinion dated Dec. 11, 2012, 6 pages.

U.S. Food and Drug Administration 510 (K) Summary for "Neurawrap", Found at: http://www.accessdata.fda.gov/cdrh_docs/pdf4/k041620.pdf.

U.S. Food and Drug Administration 510 (K) Summary for "Salutunnel", Found at: http://www.accessdata.fda.gov/cdrh_docs/pdf10/k100382.pdf.

U.S. Food and Drug Administration 510 (K) Summary for "Tendon Wrap", Found at: http://www.accessdata.fda.gov/cdrh_docs/pdf5/k053655.pdf.

U.S. Food and Drug Administration 510 (K) Summary for "SurgimeshXB", Found at: http://www.accessdata.fda.gov/cdrh_docs/pdf7/k072974.pdf.

U.S. Food and Drug Administration 510 (K) Summary for "Veritas Collagen Matrix", Found at: http://www.accessdata.fda.gov/cdrh_docs/pdf8/k083039.pdf.

U.S. Food and Drug Administration 510 (K) Summary for "Collagen Nerve Wrap", Found at: http://www.accessdata.fda.gov/cdrh_docs/pdf6/k060952.pdf.

* cited by examiner

OVERWRAP FOR NERVE STIMULATION SYSTEM

BACKGROUND OF THE INVENTION

1. Field of the Invention

The present disclosure generally relates to devices that are used in nerve stimulation. More particularly, the present disclosure relates to an overwrap for wrapping nerve stimulation electrodes, such as are used in vagus nerve stimulation.

2. Description of the Related Art

Since its introduction, nerve stimulation has been used to treat a variety of neurological conditions. Vagus Nerve Stimulation (VNS) is one type of nerve stimulation that has been used as a treatment for intractable epilepsy. Typically, this involves stimulating the left cervical vagus nerve via an implanted electrode (the vagus nerve can also be stimulated outside of the cervical area and on the right vagus). VNS has been available for clinical treatment of epilepsy in the U.S. since 1997. The therapy is achieved through an implanted pulse generator that delivers a bipolar, biphasic pulse. The implant procedure is very similar to the implantation of a pacemaker. The generator is implanted subcutaneously, typically in the upper left chest wall. An electric lead is connected between the pulse generator and the electrode using a subcutaneous tunneling tool to the vagus nerve, which lies in the carotid sheath.

Several types of nerve stimulation electrodes have been developed. These include the nerve cuff (a cylinder with an open side), which is placed around the nerve and sutured closed, and helical electrodes, which can be flexible and provide a "self-sizing" feature due to their shape. Nerve stimulation electrodes are often attached in groups. That is, two or three electrodes are attached along the nerve, and are connected to the pulse generation device via an electric lead or wire. One of the devices attached to the nerve can be an electrically inactive electrode-type device, which serves as a tether or anchor for the group of electrodes. The electric lead can be attached to this tether electrode first, thus preventing tension or stress on the lead from being transmitted to the electrically active electrodes.

Some VNS electrodes can be difficult and time consuming to attach to a nerve. Where a surgeon applies three electrode devices (two electrodes and one tether) to the nerve, each of the three elements may need to be laced around the nerve independently. Additionally, ingrowth of tissue around and between electrodes can affect their effectiveness and can significantly hinder surgical removal or other adjustment of electrodes after implantation.

It is also desirable for electrodes to provide effective nerve stimulation with minimum power consumption. However, some of the current that is applied to nerve stimulation electrodes passes into surrounding tissue, rather than being directed into the nerve.

It is believed that some nerve stimulation electrodes and electrode systems that are currently available fall short in these areas. The present disclosure is directed to overcoming, or at least reducing the effects, of one or more of the issues set forth above.

SUMMARY OF THE INVENTION

It has been recognized that it would be advantageous to develop a nerve stimulation system that is easy to install and helps reduce ingrowth of tissue around a group of electrodes It has also been recognized that it would be advantageous to develop a nerve stimulation system that promotes maximal stimulation of nerve fibers in order to achieve a therapeutic effect.

It has also been recognized that it would be advantageous to develop a nerve stimulation system that improves the efficacy of treatment while also conserving pulse generator battery power.

In accordance with one embodiment thereof, the present disclosure provides a nerve overwrap for an implantable nerve stimulation system that includes a flexible sheet of electrically insulative material, having an electrical resistivity of from about $10^8$ ohm*m to about $10^{20}$ ohm*m, adapted to wrap substantially around a group of nerve stimulation electrodes.

In accordance with a more detailed embodiment, the sheet comprises silicone. In accordance with another more detailed embodiment, the sheet has a thickness of from about 0.005 inches to 0.05 inches.

In accordance with another more detailed embodiment, the sheet has a width sufficient to extend beyond opposing end electrodes of the group of electrodes when wrapped therearound.

In accordance with another more detailed embodiment, the group of electrodes comprises at least two electrically active electrodes, spaced a first distance from each other, and the sheet has a width that is at least 2.5 times the first distance. In accordance with another more detailed embodiment, the group of electrodes comprises at least two electrically active electrodes and one electrically inactive electrode, the active electrodes being spaced a first distance from each other, and the sheet has a width sufficient to extend beyond opposing end electrodes of the group of electrodes by a distance of about 0.2 inches to 1 inch when wrapped therearound.

In accordance with another more detailed embodiment, the sheet has opposing ends configured to be sutured together. In accordance with another more detailed embodiment, the sheet includes a flange, extending from one end of the sheet, configured for attachment to the opposing end when the sheet is wrapped around the group of electrodes on the nerve.

In accordance with another more detailed embodiment, the sheet is biased toward a substantially cylindrically wrapped configuration, defining a resilient encasement of flexible size. In accordance with another more detailed embodiment, the sheet includes first and second flanges, extending from opposite ends of the sheet, the flanges positioned to come into mating contact when the sheet is in the substantially cylindrically wrapped configuration.

In accordance with another more detailed embodiment, the sheet includes electrodes and an electrical lead attached to the electrodes, integrated into the overwrap sheet, the electrodes positioned on an inner surface of the sheet and having a substantially complete circular extent when the sheet is in the substantially cylindrically wrapped configuration.

In accordance with another more detailed embodiment, the sheet includes a mechanical interlocking device, adapted to mechanically connect opposing ends of the sheet together when wrapped around the electrodes. The mechanical interlocking device can be selected from the group consisting of: an elongate tab and slot mechanism, a plurality of protrusions and slots, and a strap and slot device.

In accordance with another more detailed embodiment, the sheet has a preformed shape defining a closeable pocket for surrounding the electrodes.

In accordance with another embodiment thereof, the present disclosure provides an implantable nerve stimulation system. The system includes a pulse generation device, suitable for subcutaneous implantation into a body; a group of electrodes, electrically connected to the pulse generation device, and configured for attachment along a nerve; and an overwrap, comprising a flexible sheet of electrically insulative material, having a resistivity of from about $10^8$ ohm*m to about $10^{20}$ ohm*m, configured to wrap substantially completely around the group of electrodes.

In accordance with yet another embodiment thereof, the present disclosure provides a method for implanting a nerve stimulation system. The method includes the steps of attaching at least two stimulation electrodes along a common nerve, wrapping a single flexible sheet of insulative material, having an electrical resistivity of from about $10^8$ ohm*m to about $10^{20}$ ohm*m, around the at least two electrodes, and attaching opposing ends of the sheet together so as to substantially completely encase the electrodes.

These and other embodiments of the present disclosure will be discussed more fully in the description. The features, functions, and advantages can be achieved independently in various embodiments of the claimed invention, or may be combined in yet other embodiments.

Figure 1:
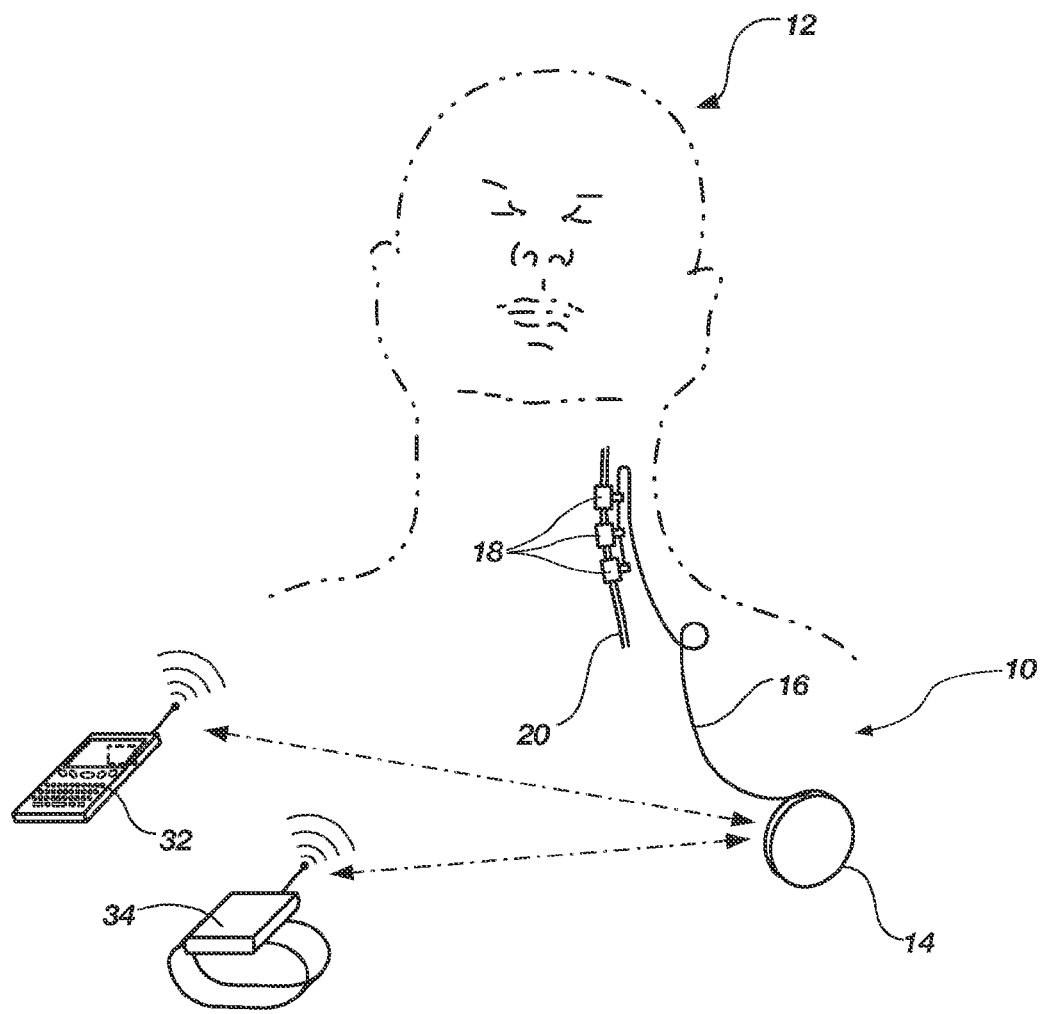
FIG. 1 is a schematic representation of a human subject showing a subcutaneous vagus nerve stimulation system, having a lead extending from a battery-powered pulse generator device to electrodes attached at the left vagus nerve.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the spirit and scope as defined by the appended claims.

DETAILED DESCRIPTION

Illustrative embodiments are described below as they might be employed in a nerve overwrap for nerve stimulation electrodes. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Further aspects and advantages of the various embodiments will become apparent from consideration of the following description and drawings. These embodiments are described in sufficient detail to enable those skilled in the art to practice the invention, and it is to be understood that modifications to the various disclosed embodiments may be made, and other embodiments may be utilized, without departing from the spirit and scope of the present invention. The following detailed description is, therefore, not to be taken in a limiting sense.

As used herein, the term "implantable" means a device that can be completely implanted into a human or animal body, with no portions of the apparatus extending outside the body after implantation.

As used herein, the terms "implantable device" and "implantable medical device" or "IMD" mean any type of electrical device that is implantable into a human or animal body, and is configured to monitor or affect a function of the body. Examples of implantable medical devices include cardiac pacemakers, nerve stimulation devices, and implantable drug delivery devices.

Shown in FIG. 1 is a schematic diagram of one embodiment of an implantable vagus nerve stimulation system, indicated generally at 10, implanted into a patient 12. The system includes a pulse generator 14, and a tether or lead 16 that has one or more electrodes 18 at its distal end. The tether and electrodes are collectively referred to as the lead, and the lead provides an interface between the pulse generator 14 and the electrodes 18. The electrodes 18 are attachable to the vagus nerve 20.

Figure 2:
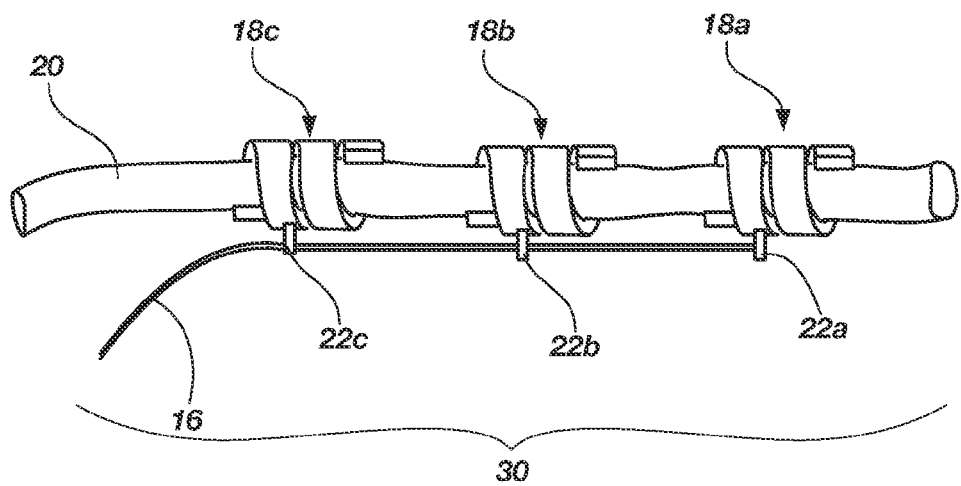
FIG. 2 is a pictorial representation of a group of two helical stimulation electrodes and one anchoring helix attached along a nerve in one embodiment of a nerve stimulation system.

A pictorial representation of a distal end section of a lead 30 in one embodiment of a nerve stimulation system is provided in FIG. 2. In this embodiment, the lead includes three helical devices 18a-c attached axially along a nerve 20. Each of the helical devices is interconnected to the pulse generation device (14 in FIG. 1) via the tether 16. This embodiment includes two helical electrodes 18a, 18b, and a third helical device 18c that is electrically inactive, but which is attached to the tether and provides additional support to anchor the electrodes to the nerve. Each of the helices includes a post, labeled 22a-c, which mechanically connects the respective helix to the tether 16. In the electrically active helices (18a, b), this post is also an electrical conductor, which extends through the substrate of the helix and connects to the conductor portion of the electrode (not shown) on the inner surface of the helix, to transmit electrical pulses thereto. For the third helix, 18c, the post provides a mechanical connection only, not an electrical connection, serving to anchor the electrodes better to the nerve. This third anchoring helix 18c may be longer than helices 18a and 18b to anchor lead 30 to the nerve more securely. In another embodiment, helix 18c can also be an electrically conductive electrode.

It is to be understood that the illustration of three helices attached to the nerve is only one of many possible embodiments of a nerve stimulation system. Various numbers of electrodes (e.g., three, four, five, or more) can be used to stimulate the nerve, if desired. Moreover, it is to be understood that the helical electrodes illustrated and described herein are only one type of electrode that can be used in conjunction with the overwrap system disclosed herein. Other types of electrodes, such as cuff-type electrodes, can also be used. In vagus nerve stimulation, the electrodes can be attached to the mid-cervical portion of the vagus nerve, inferior to the cardiac branches of the left vagus nerve. However, other attachment sites can also be used, such as the right vagus, near the cardiac plexus, or other nerves aside from the vagus large enough to wrap an electrode around.

Referring back to FIG. 1, while these features are not shown, the pulse generator 14 typically includes within its housing a microprocessor with digital memory, and a battery (e.g. a rechargeable battery) for providing electrical power to the device. The pulse generator can also include a wireless transmitter and an antenna for transmission of signals to an external device, and a GPS transceiver, if desired, for obtaining locational information. The transmitter and antenna can be configured to send and/or receive data and programming and control instructions from an external communications device, such as a smart phone or PDA-type device 32 or a wristwatch-type device 34. These and other types of external devices can be configured to wirelessly send and receive data and programming instructions with the implanted device, such as using Bluetooth or some other wireless transmission protocol, allowing the external device to receive and transmit date, and perform power-intensive computational operations, so as to conserve power of the implanted device. The external devices can also be in communication with other external systems, such as a cellular communications system or GPS satellite system, for example.

The pulse generator 14 can be a multi-programmable device, which allows a physician to set various parameters of operation of the device. The programmable parameters can include signal amplitude (e.g., 0-3.5 mA), frequency (e.g., 1-30 Hz), pulse width (e.g., 130-1000 µs), signal ON time (e.g., 7-60 sec) and signal OFF time (e.g., 0.2-180 min). It is to be appreciated that these pulse parameters are only exemplary, and that other parameters can also be used. The pulses can be delivered at the specified amplitude and frequency over the course of the ON time, and then during the OFF time, no stimulation takes place. This type of device typically does not stimulate continuously because it has been found that the antiepileptic effect tends to last much longer than the actual time of stimulation. In one embodiment, pulse settings can be 2 mA, at 15 Hz frequency, 250 µs pulse width, with a 30 sec ON time, and 5 min OFF time. The variability in parameters allows the physician to adjust for greater efficacy or less severe side effects, depending on the patient. An implantable VNS system of this type and having these basic features is known to those of skill in the art, and is commercially available, such as from Cyberonics, Inc. of Houston, Tex.

Figure 3:
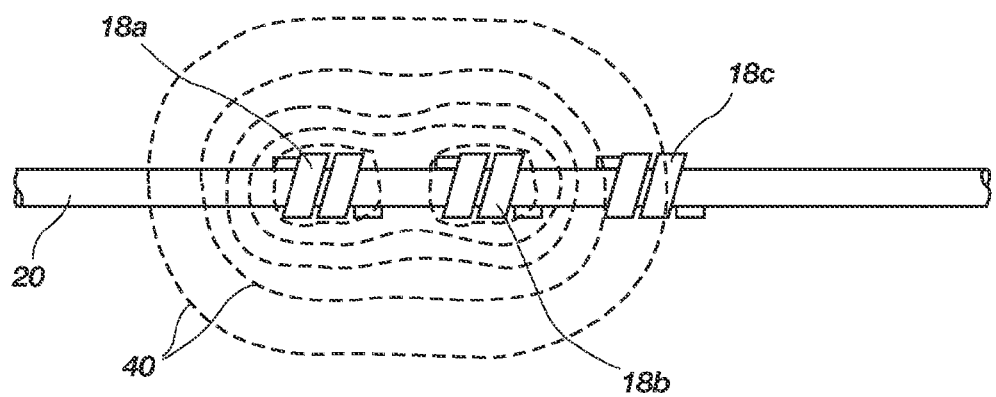
FIG. 3 is a plan view of a group of electrodes attached along a nerve, showing field lines that illustrate the spreading of electrical energy into tissue surrounding the nerve.

As noted above, ease of implantation of VNS electrodes, tissue ingrowth and ease of removal, and current loss to surrounding tissue are among issues that are of concern with respect to VNS systems. Advantageously, as disclosed herein, apparatus and methods have been developed that address these concerns. Disclosed herein is a nerve overwrap for a VNS system that is relatively easy to implant, minimizes the positional variability of the electrodes, inhibits tissue ingrowth, and helps concentrate current that is injected into the nerve. FIG. 3 illustrates the challenge of current spreading or leakage into surrounding tissue. As shown in this figure, a group of nerve stimulation electrodes 18a-c are attached along a nerve 20. This group includes two electrically active helixes, 18a, b, and one tether helix 18c, which is not electrically active. When current is provided to the stimulation electrodes 18a, b, a substantial quantity of electrical current is lost to surrounding tissue, as indicated by the electrical field lines 40. From this figure it can be seen that a significant quantity of electrical energy extends into tissue surrounding the electrodes. This is essentially lost energy, since current injected into tissues surrounding the nerve has no therapeutic effect. Additionally it is believed that current flowing into the surrounding tissues could contribute to stimulation related side effects. Specifically, it could stimulate local muscle fibers causing the muscles in the neck to twitch during stimulation. Also, nearby nociceptor neurons may be stimulated, resulting in painful stimulation. This reduces the proportion of current that is injected into the nerve, thus requiring more overall current to be used to obtain the desired therapeutic effect. With implantable devices, it is desirable to minimize the current required, so as to conserve battery resources.

Figure 4:
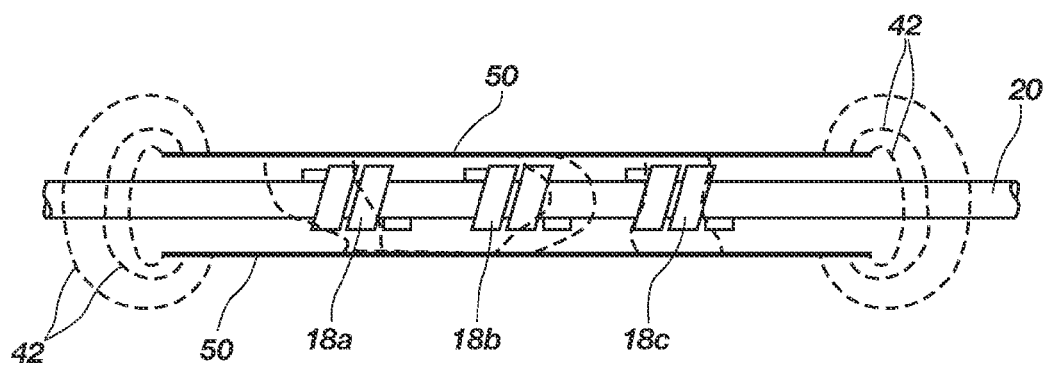
FIG. 4 is a plan view of the electrodes of FIG. 3, showing field lines that illustrate the effect of a nerve wrap placed around the group of electrodes.

It has been determined that an insulative material, wrapped around a group of stimulation electrodes attached to a nerve, can significantly reduce current leakage into surrounding tissues, and increase current injection into the nerve. This is illustrated in FIG. 4. Like FIG. 3, a group of nerve stimulation electrodes 18a-c, including two electrically active helixes 18a, b, and one electrically inactive tether helix 18c, are attached along a nerve 20. In this case, however, an insulative nerve overwrap 50 is wrapped around the group of electrodes, and significantly reduces the quantity of electrical current that is lost to surrounding tissue, as indicated by the more attenuated electrical field lines 42. This configuration decreases current loss and increases the proportion of current that is injected into the nerve 20, thus conserving battery resources. The electrically insulative properties of the overwrap 50 reduce the amount of current that is lost into surrounding tissue, and also concentrates the electric field around the nerve 20, thus concentrating the current that is injected into the nerve and increasing the electrical efficiency of the VNS system. It has also been found that use of an insulative nerve overwrap also helps reduce tissue ingrowth, and helps to stabilize the position of the electrodes 18.

Figure 5:
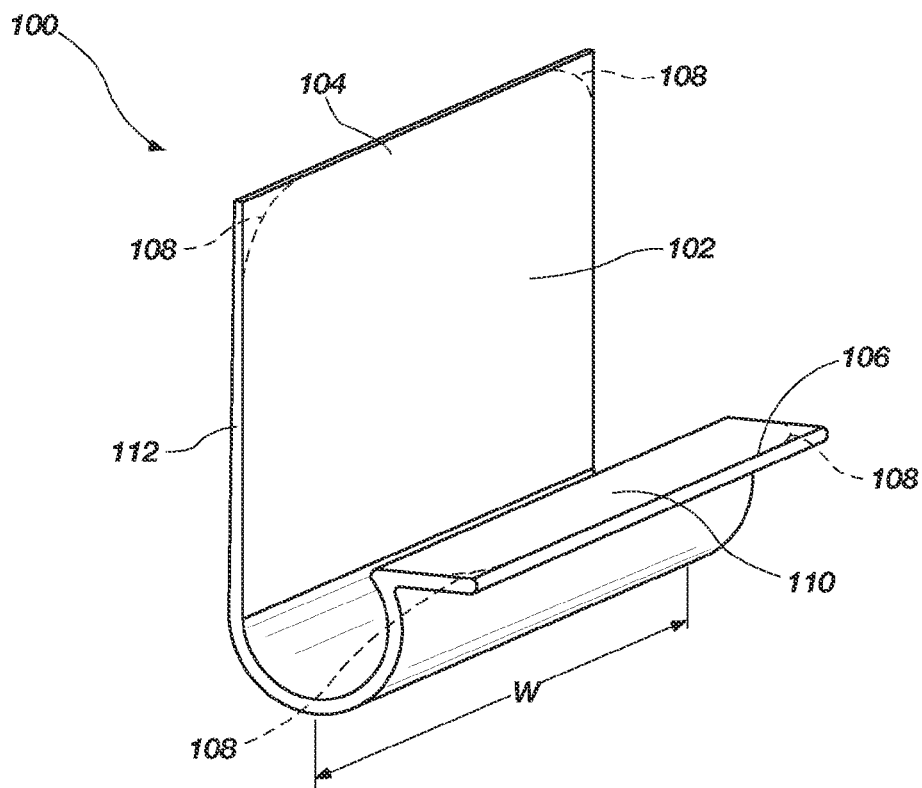
FIG. 5 is a perspective view of one embodiment of a nerve overwrap configured to be wrapped around a group of electrodes in accordance with the present disclosure.
Figure 6:
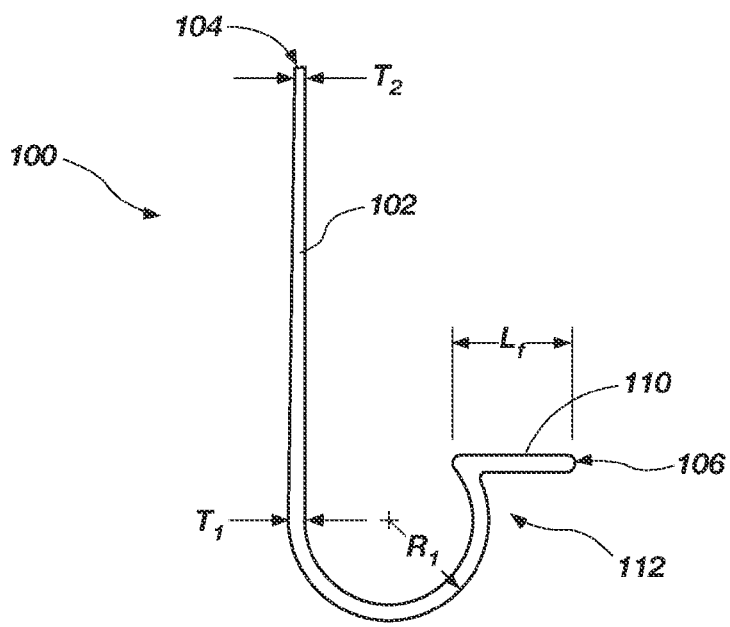
FIG. 6 is a side edge view of the nerve overwrap of FIG. 5.

Shown in FIGS. 5 and 6 are two views of an embodiment of a nerve overwrap 100 configured to be wrapped around a group of electrodes. The nerve overwrap is a sheet 102 of electrically insulative material, configured to wrap substantially completely around a group of electrodes attached to a nerve. In this embodiment the sheet has opposing ends 104, 106, configured to be sutured together. There are a variety of insulative materials that can be used. In one embodiment, the sheet is of silicone, such as silicone elastomer MED-4750 manufactured by NuSil. Other insulative materials, such as polytetrafluoroethylene (PTFE), polyethersulfone, collagen, poly-amino acids, silks, elastins, polyester, polyether, poly-4-hydroxybutyrate (P4HB), or other similar materials can also be used.

The sheet has a length, measured along the front edge 112 in FIG. 5, sufficient to wrap around the group of electrodes, with opposing ends 104, 106 of the sheet configured to attach to each other. The length and width W of the sheet can vary, as can its shape and configuration, as discussed in more detail below. It is believed that insulative sheets in accordance with the present disclosure can have a length in the range of 0.75 in to 2 in, and a width of 1 inch to 3 inches. In one embodiment, an insulative sheet that is 1.5 inches long and 1 inch wide has been used. The primary factors that influence the size of the sheet are the length of the electrodes, ease of handling during implant, the size of the incision, and the length of the exposed nerve. The insulative sheet can also be provided with rounded corners 108, so as to ease implantation and to reduce potential damage to surrounding tissues.

In the embodiment of FIGS. 5 and 6, the insulative sheet 102 includes a flange 110, extending from one end 106 of the sheet. This flange is configured for attachment to the opposing end 104 of the sheet when the sheet is wrapped around the group of electrodes on the nerve. That is, to wrap the overwrap around the electrode group, the surgeon pulls the top portion of the overwrap 104 over until it lies upon the flange 110, where it is sutured together. The flange thus provides an easily accessible area for secure attachment of the opposing ends of the nerve overwrap. To serve this purpose, in the embodiment of FIGS. 5 and 6 the flange can have a length $L_f$ of from 0.07 inches to 0.3 inches long.

The nerve overwrap sheet 102 can be biased toward a substantially cylindrically wrapped configuration. That is, the sheet can be formed to naturally rest in the curved "J" shape shown in FIGS. 5 and 6. This facilitates implantation because it requires less effort on the part of an implanting surgeon to bend the overwrap into the cylindrical shape, since the overwrap naturally has an approximately 180° curve of radius $R_1$, already built in. Methods for producing sheets of silicone material with a pre-biased shape, such as by injection molding and extrusion are well known to those of skill in the art.

Figure 7A:
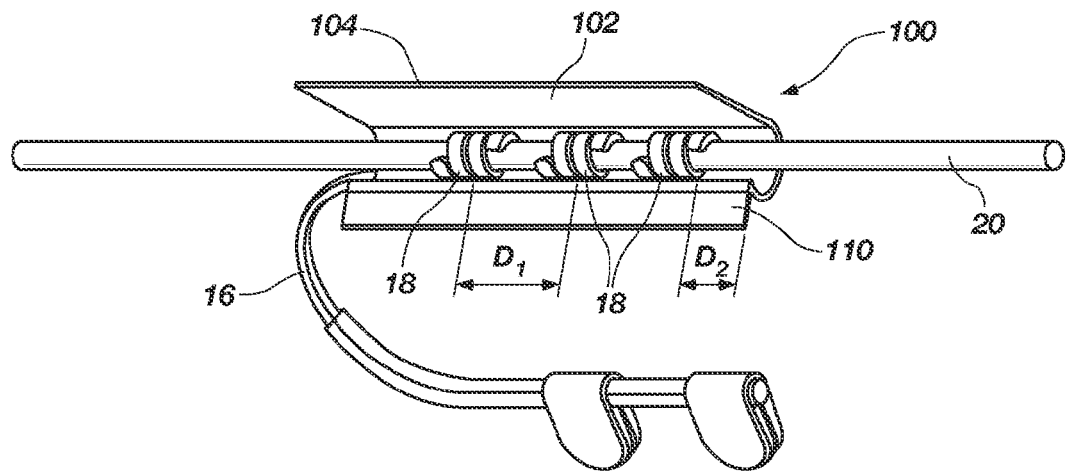
FIGS. 7A-C are a sequence of perspective views showing a nerve overwrap like that of FIG. 5 being attached around a group of helical stimulation electrodes positioned along a nerve.
Figure 7B:
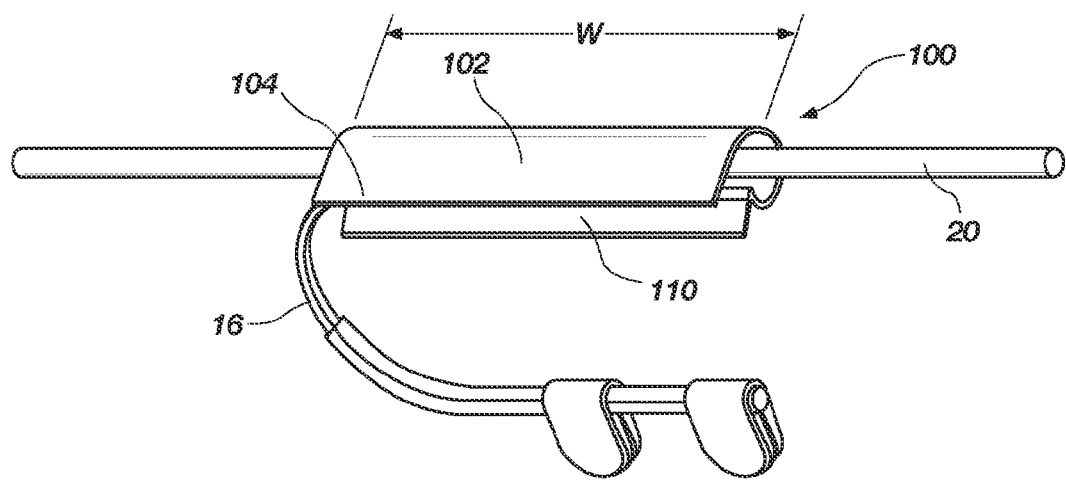
Figure 7C:
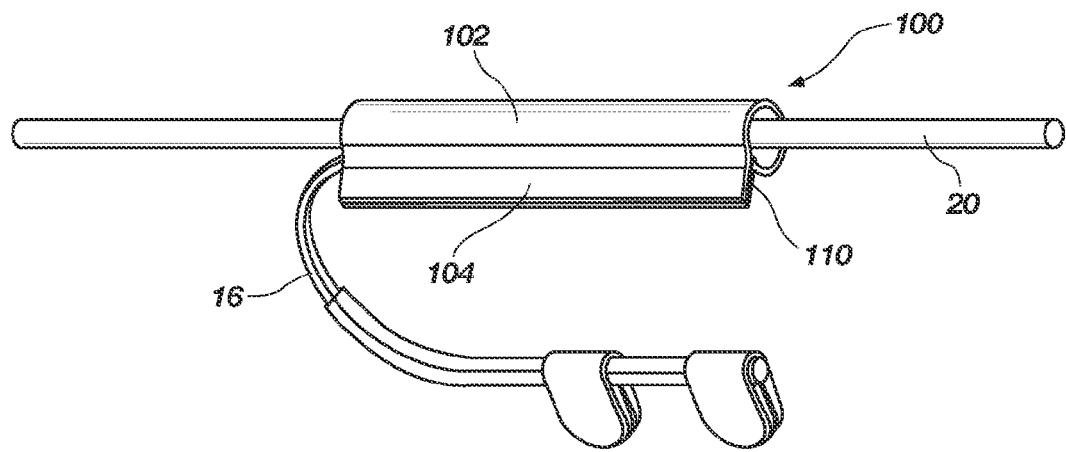

Shown in FIGS. 7A-C are a series of perspective views of a nerve overwrap 100 like that of FIG. 5 being wrapped around a group of helical stimulation electrodes 18 positioned along a nerve 20. Implantation of the VNS system with a nerve overwrap generally involves attaching at least two stimulation electrodes along a common nerve, attaching the electrical lead 16 to them, and then wrapping the insulative nerve overwrap sheet 102 around at least two electrodes. Attaching the electrodes generally involves separating the nerve fiber from surrounding tissue, so that the electrodes can be placed around the nerve. Once the electrodes are in place, the surgeon inserts the free end 104 of the nerve overwrap under the nerve, wraps it back around and sutures the free end to the overwrap flange 110. It is believed that 3-5 sutures or a running stitch are generally sufficient to securely fasten the ends of the overwrap together.

The diameter of the wrap in its implanted configuration also affects current spread. It is desirable that the nerve overwrap be snug around the nerve, but not so tight as to constrict or put pressure on the nerve. In general, smaller diameters are believed to be most effective. However, if the wrap is too tight, there is a possibility of constricting the nerve. In general, it is believed that to provide a desired snugness, the inside diameter of the wrap can be from about 105% to about 200% of the outside diameter of the electrodes.

As shown in FIG. 6, the thickness of the sheet can vary. Generally, the thickness of the sheet can vary from about 0.005 inches to 0.02 inches. The sheet thickness is primarily dependent upon the mechanical properties of the material and practical considerations, such as flexibility, ease of use, and durability. If the sheet is too thick it may be relatively inflexible and difficult to implant. If the sheet is too thin, it can tear during implantation or handling, or may degrade too easily after implantation. In the embodiment shown in FIGS. 5 and 6, the sheet has a maximum thickness $T_1$ of about 0.02 inches in the flange and bottom curve region of the nerve overwrap, indicated generally at 112, and tapers to a minimum thickness $T_2$ of about 0.01 inches toward the top of the free edge 104. In another embodiment, the sheet does not taper (i.e., $T_1$ equals $T_2$). As noted above, the width W of the sheet 102 can vary.

In order to help reduce current spreading, it is believed to be desirable that the sheet has a width W that is at least sufficient to cover the active electrodes. In the embodiment of FIGS. 7a-c, the group of electrodes includes two electrically active electrodes 18a, b, and one electrically inactive electrode 18c. The active electrodes are adjacent to and are spaced a first distance $D_1$ from each other. In this configuration, it has been found desirable that the sheet 102 have a width W that is at least 2.5 times that first distance (i.e. W≥2.5*$D_1$).

Moreover, it is considered desirable that the sheet cover the active electrodes and also provide some amount of overhang $D_2$ beyond them. Further, in order to help stabilize the entire group of electrodes and further reduce problems associated with tissue ingrowth, it is desirable that the sheet cover all of the electrode devices attached to the nerve, and provide some amount of overhang beyond the end of the exterior electrodes. The overhang $D_2$ of the nerve overwrap can relate to its electrically insulative properties, which are desirable for reducing electrical losses and power usage in a nerve stimulation system, while still providing effective stimulation. It is believed that a suitable overhang $D_2$ is in the range of 0.2 inches to 1 inch. In one embodiment, assuming electrodes having a spacing of 0.3 inches, a suitable overhang will be provided by a nerve overwrap having a total width W of 1.2 inches. In general, it is believed that a wider wrap is better at reducing current spread. Given the considerations presented above, an effective range could be between about ⅓ shorter than the total width presented above, and about 75% longer than that width.

As is well known, electrical insulation is essentially the same as electrical resistance, and is the opposite of conductance. Different materials provide different levels of resistance to electrical current, with some materials being good conductors and others being good resistors or insulators. In general, it is believed desirable that the nerve overwrap material have a resistivity in the range of from $10^8$ ohm*m to $10^{20}$ ohm*m. Additionally, in order for the overwrap material to stay within the desired range of resistivity after implantation in the body, it is desirable that the overwrap material be non-porous, so that it will not soak up fluids or ion solutions, and not degrade within the body. Flexible silicone materials that are commercially available can provide electrical resistance in this range, and are also non-porous and resistant to degradation within the body. In addition to silicone, other insulative materials are available that have the desired durability for this application, and also have a resistance in the desired range (e.g., polytetrafluoroethylene (PTFE) or polyethersulfone).

As noted above, the thickness of the nerve overwrap sheet is primarily dependent upon mechanical and practical considerations, not electrical properties. It is believed that the thickness of the overwrap material does not significantly affect current spreading. Given the range of resistivities listed above, if a wrap were created thin enough to significantly affect the current spread, it is believed that it would probably not have the desired mechanical properties.

Figure 8:
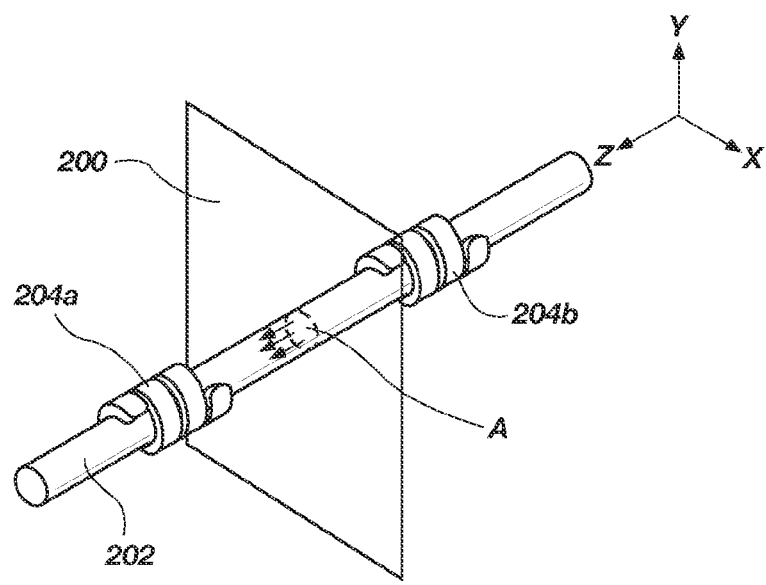
FIG. 8 is a perspective diagram which conceptually illustrates how current flowing in a nerve is calculated.

Current flowing in the nerve when provided with a nerve overwrap as disclosed herein has been modeled. Viewing FIG. 8, the total current flowing along a long axis z of a nerve 202 and through a cross-section A taken along an imaginary plane 200 that is substantially perpendicular to the long axis of the nerve and between two stimulating electrodes 204*a, b* can be represented by the following equation:

$$I_Z = \int_A J_Z * dA \qquad [1]$$

In this equation, $I_Z$ is the total current flowing along the z axis of the nerve, and $J_Z$ is the current density vector in the z direction. $I_Z$ can be used as an indication of increased current flowing into the nerve. However, due to the directional dependence (i.e., the current flowing normal to the plane 200), it is not a direct measure of the total current flowing into the nerve, and an increase in $I_Z$ may indicate not only increased current into the nerve but also a change in the direction of the current flow. Using this computational model, it has been found that wrapping the electrodes with an insulative wrap should provide about a 3600% increase in axial current through the nerve. The total current flowing into the nerve is believed to increase by a lesser amount, but the increase in axial current flow is an indication that less current is lost to the surrounding tissues. This calculation from the computational model is relatively simple and straightforward to do, though it is believed by some that this quantity may not be applicable in-vivo or in bench trials. However, it is believed that the total current through the nerve could possibly be measured in a bench trial, such as by using a small, sensitive and accurate current probe, looped around a nerve or nerve stimulant between two stimulating electrodes.

Figures 9A, 9B:
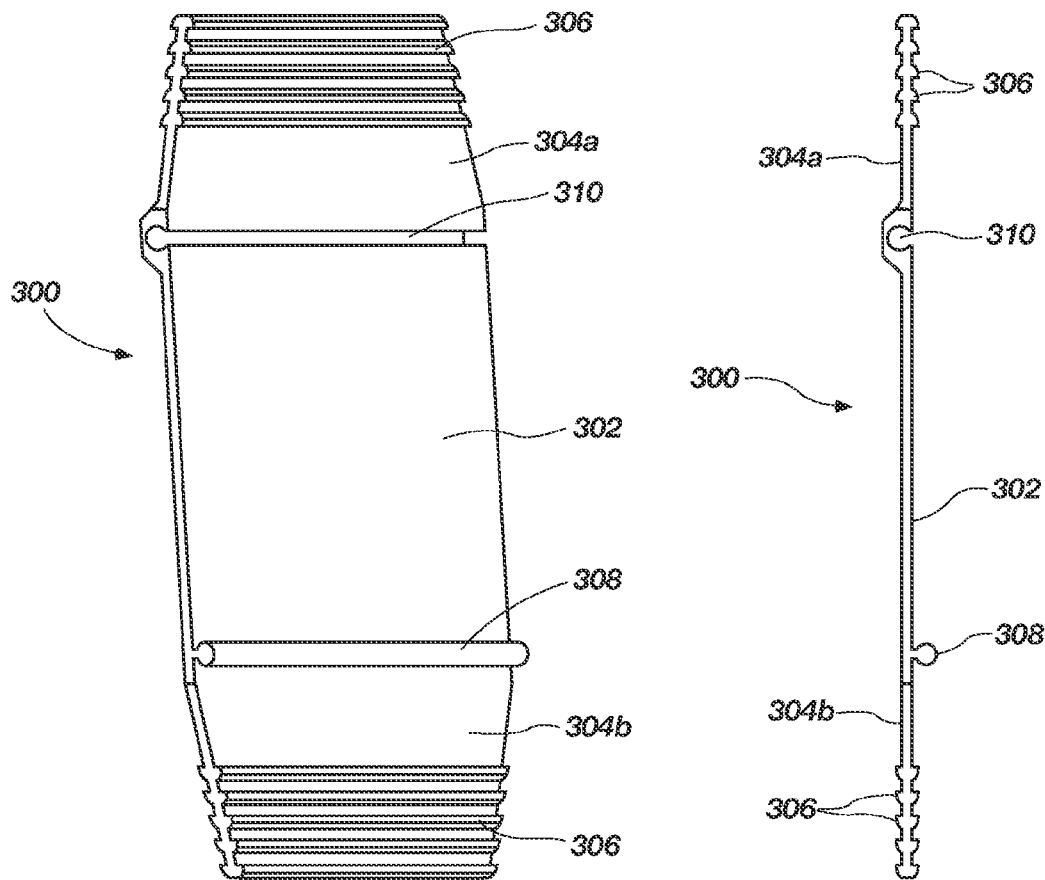
FIGS. 9A-B are perspective and side edge views of another embodiment of a nerve overwrap that is generally sheet-like, configured to be wrapped around a group of electrodes in accordance with the present disclosure.

The shape, size and configuration of the nerve overwrap can vary. Shown in FIGS. 9-15 are perspective views of additional embodiments of nerve overwraps in accordance with the present disclosure. Shown in FIGS. 9A-B are perspective and side edge views of a nerve overwrap embodiment 300 that provides a substantially flat sheet 302 having distal flanges 304*a, b* with ribs 306, and an interlocking tab 308 and slot 310. The flexible sheet 302 is configured to be wrapped around a nerve and a group of electrodes thereon, with the distal flanges 304*a, b* attached together. The interlocking tab 308 and slot 310 are configured to function similar to a zipper storage bag, allowing a surgeon to fasten the wrap around the group of electrodes by pressing the tab into the slot along its length during implantation. Once the nerve overwrap 300 is fastened around the nerve and electrodes, a few sutures can be tied through the flanges 304 to ensure a strong attachment that will not come apart within the body. The distal flanges 304 of the overwrap can include exterior ribs 306, which make it easier for a surgeon to grasp the nerve overwrap during implantation, and can provide structure against which the sutures can be tied.

Figure 10A:
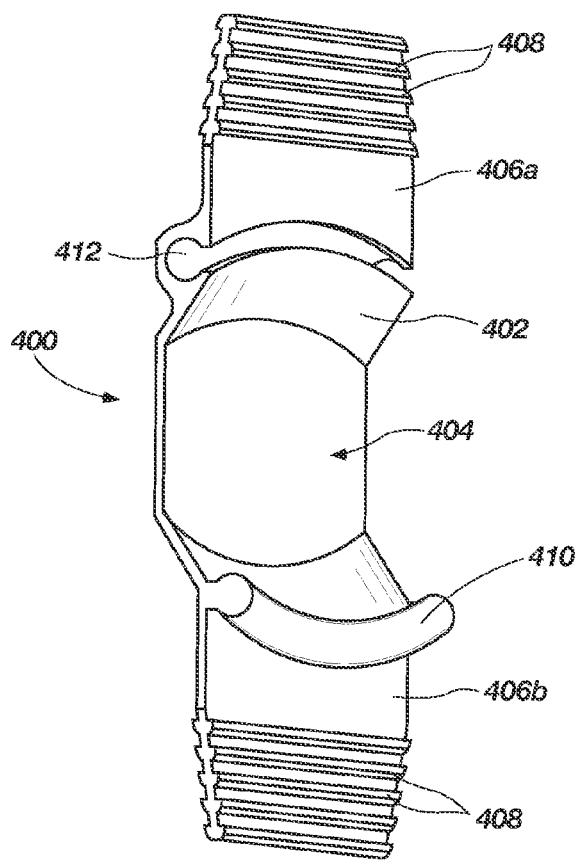
FIGS. 10A-B are perspective and side edge views of another embodiment of a nerve overwrap that has a preformed shape, configured to be wrapped around a group of electrodes in accordance with the present disclosure.
Figure 10B:
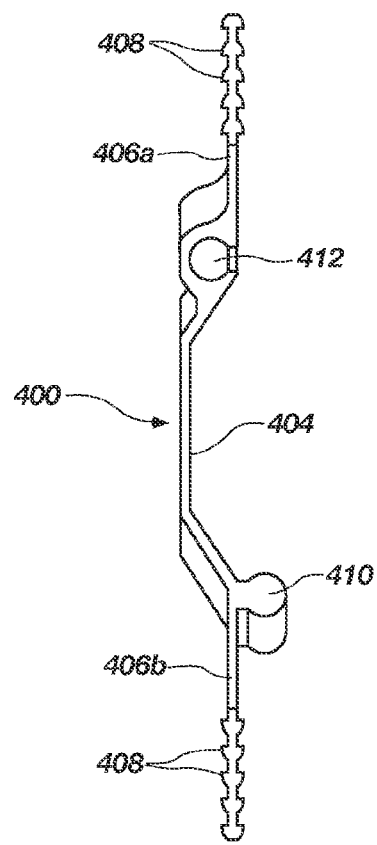
Figure 11A:
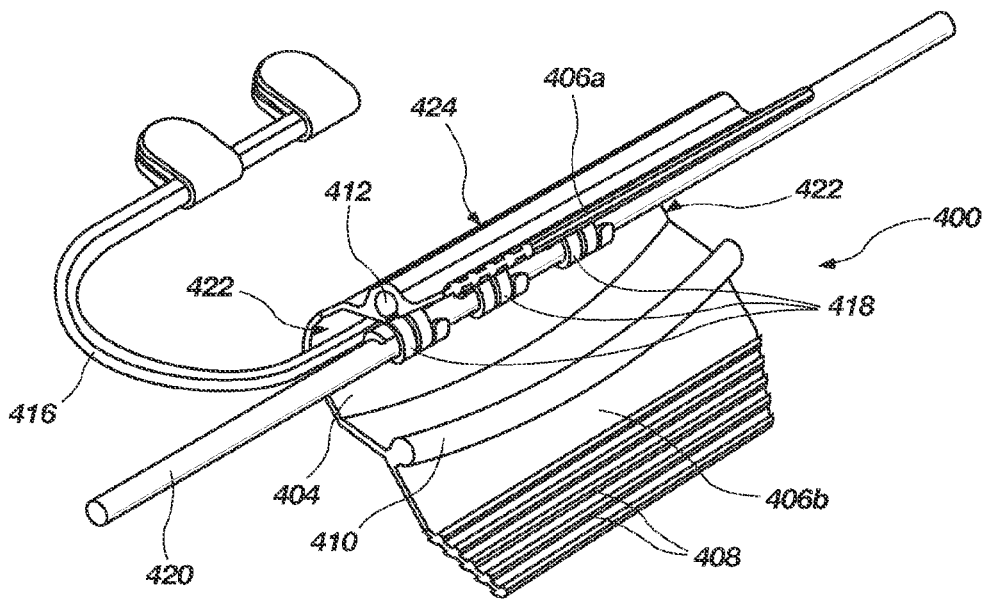
FIGS. 11A-B are a sequence of perspective views showing a nerve overwrap like that of FIG. 10 being attached around a group of helical stimulation electrodes positioned along a nerve.
Figure 11B:
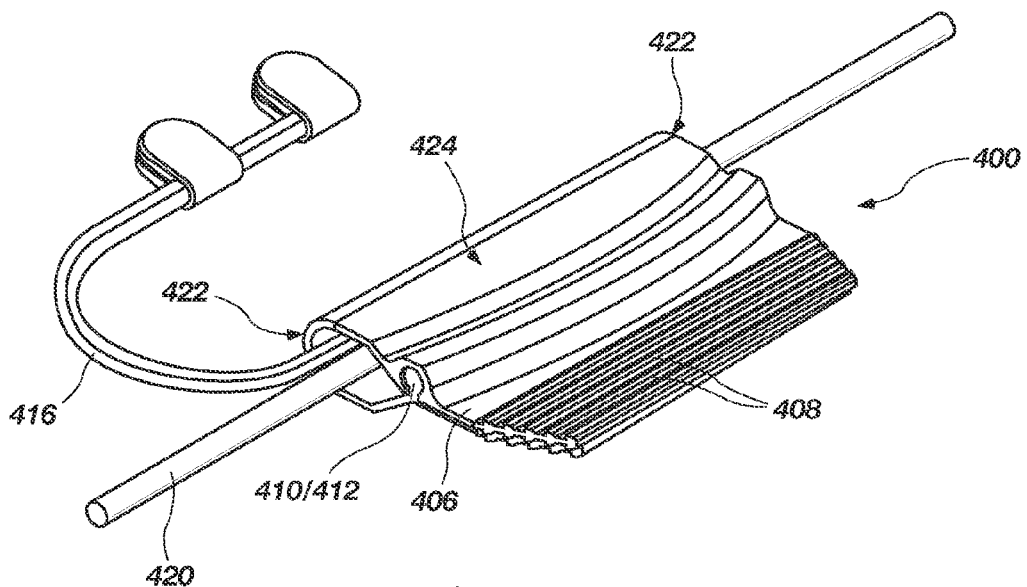

Another embodiment of a nerve overwrap 400 is shown in FIGS. 10A-B. This embodiment comprises a sheet 402 of insulative material that, rather than being flat, is pre-formed or shaped with a central pocket region 404. Like the embodiment of FIGS. 9A-B, this nerve overwrap includes a pair of distal flanges 406*a, b* with ribs 408, and an elongate interlocking tab 410 and slot 412 for connecting the device together when wrapped around the nerve and electrodes. Shown in FIGS. 11A-B are a sequence of perspective views showing the nerve overwrap 400 of FIG. 10 being attached around a group of helical stimulation electrodes 418 connected to a lead 416 and positioned along a nerve 420. The central pocket region 404 is formed to have a longitudinal taper, so that when wrapped around a group of electrodes, the circumference of the cylindrical wrapped portion is smaller at the ends 422, and larger in the center 424. This helps mechanically stabilize the wrap and the electrodes, and also reduces the size of openings at the ends of the overwrap, which can help further limit tissue ingrowth. As with the embodiment of FIGS. 9A-B, the interlocking tab 410 and slot 412 configuration allows a surgeon to fasten the wrap around a group of electrodes and attach the flanges together similar to the way that zipper storage bags are sealed, after which the flanges can be sutured together.

Figures 12A, 12B:
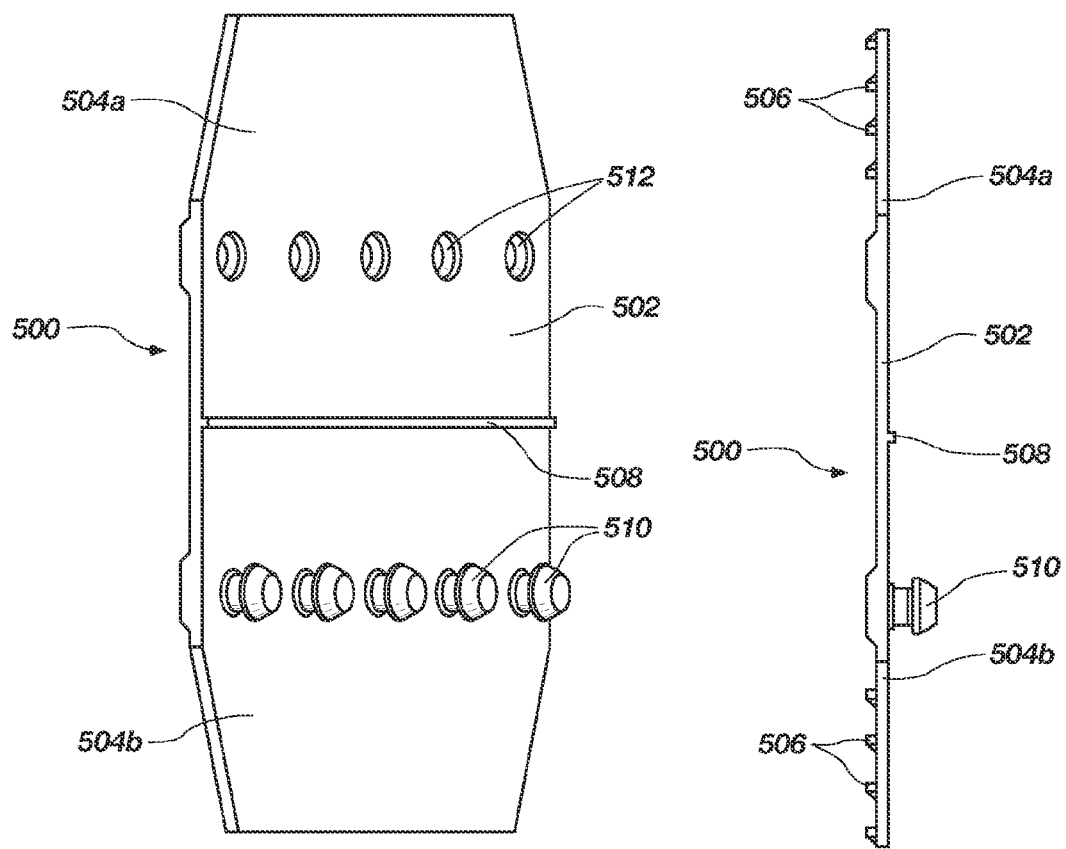
FIGS. 12A-B are perspective and side edge views of another embodiment of a sheet-like nerve overwrap with interlocking buttons, configured to be wrapped around a group of electrodes in accordance with the present disclosure.

FIG. 12A-B are perspective and side edge views of another embodiment of a nerve overwrap 500 configured to be wrapped around a group of electrodes in accordance with the present disclosure. This embodiment provides a substantially flat, flexible sheet 502 having distal flanges 504*a, b* with ribs 506. A central rib 508 helps assist alignment of the device for wrapping around an electrode group. This embodiment includes, on an interior side of the sheet toward one end flange 504*b*, a group of protuberances or buttons 510, which are configured to press though and interlock within corresponding holes or slots 512 that are provided in the opposing flange 504*a*. These structures function similar to buttons or the like, for mechanically fastening the nerve overwrap 500 around an electrode group. Once the flanges 504 of the overwrap are fastened in this way, a surgeon can provide sutures through the flanges, if desired.

Figure 13:
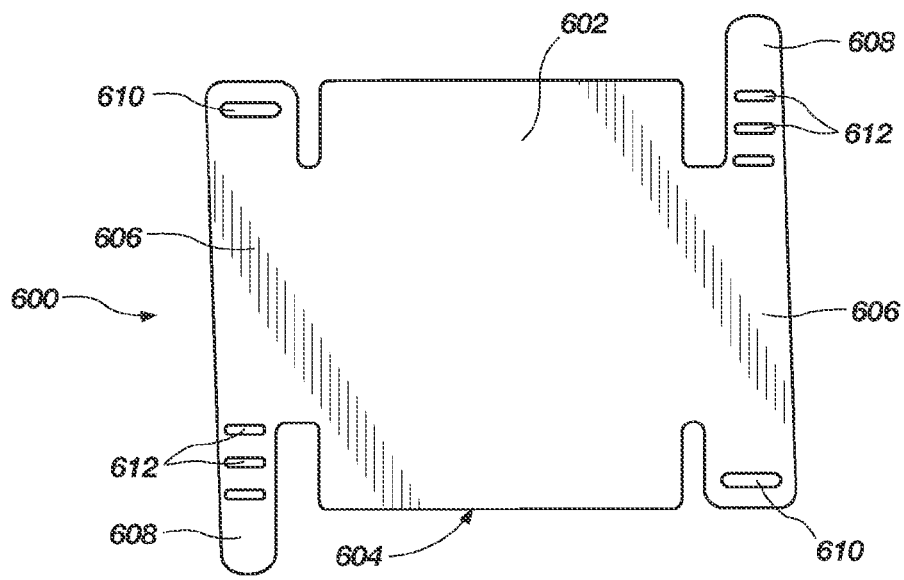
FIG. 13 is a plan view of another embodiment of a sheet-like nerve overwrap with a strap and slot attachment design, configured to be wrapped around a group of electrodes in accordance with the present disclosure.

Shown in FIG. 13 is a plan view of yet another embodiment of a nerve overwrap 600. This embodiment provides a substantially flat sheet 602 of flexible material, having a central wrap portion 604, and end sections 606*a, b*, each with a strap 608 and a slot 610. Each end section or portion 606 of the sheet includes a strap or tab 608 with locking ribs 612, and a corresponding slot 610. For implantation, the surgeon wraps the central portion 604 around an electrode group, then slides each strap 608 through the corresponding slot 610 to obtain the desired tightness of the wrap. As the straps are fed through the slots, the locking ribs 612 will interlock with the edges of the corresponding slots 610, like tabs on a belt. The surgeon can thus pull the tabs 608 to provide the desired level of snugness of the overwrap.

Figure 14:
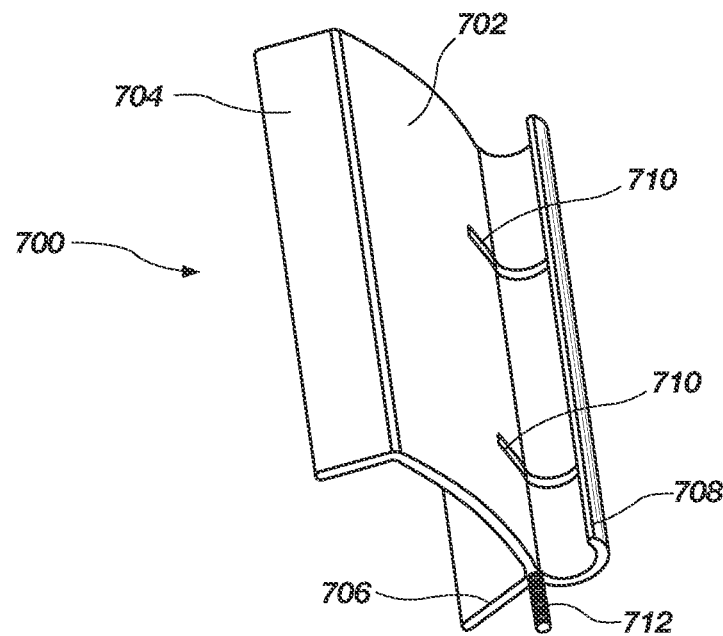
FIG. 14 is a perspective view of an embodiment of a nerve overwrap having integral electrodes in accordance with the present disclosure, the nerve overwrap being in an opened configuration.
Figure 15:
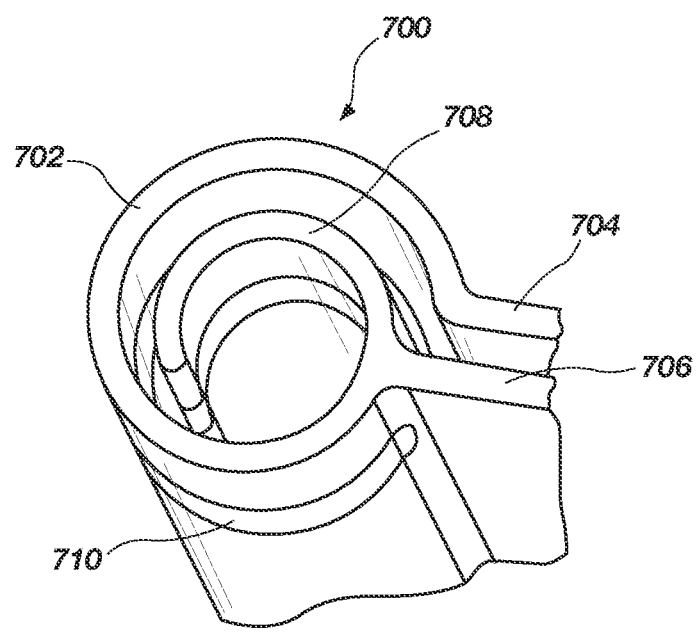
FIG. 15 is a perspective view of the nerve overwrap with integral electrodes of FIG. 14, the nerve overwrap being in a closed configuration.

Another embodiment of a nerve overwrap is provided in FIGS. 14 and 15. This embodiment provides a self-wrapping nerve overwrap 700 with integral electrodes. In FIG. 14 this embodiment of the nerve overwrap is in an opened configuration, and in FIG. 15 it is in a closed configuration. This embodiment includes a central body portion 702, with a top flange 704, a bottom flange 706, and a curved insert tab portion 708. The overwrap device is formed of flexible, electrically insulative material that has a preformed cylindrical shape, to which it is naturally biased. The material can be unrolled and flattened out from this shape, as shown in FIG. 14, but when released will naturally tend to return to the cylindrical shape, as shown in FIG. 15. When in the coiled cylindrical shape, the insert tab 708 fits inside the cylinder, and the top and bottom flanges 704, 706 come substantially into flat abutment.

In this embodiment, electrodes 710 and the other components that make up the VNS lead are integrated into the central body portion of the self-wrapping nerve overwrap. The lead 712 is incorporated into the body portion 702 by over-molding or some other suitable manufacturing method. The self-wrapping overwrap provides a mechanism to hold the integrated lead electrodes 710 in direct contact with the vagus nerve.

The self-wrapping nerve overwrap 700 wraps the electrodes 710 completely around the nerve and simultaneously provides electrical insulation to reduce current leakage and promote current injection into the nerve. The orientation or shape of the electrodes 710 can vary. As shown in FIGS. 14 and 15, the electrodes 710 can be substantially straight with respect to the lateral edges of the nerve overwrap, thereby gaining a circular or helical shape around the nerve when the overwrap is attached. Alternatively, rather than a straight configuration, the electrodes can be a continuous "W" shape or other unique shapes (not shown) to maximize contact with the nerve. The electrodes 710 may vary in size and shape, while still providing substantially complete circumferential (i.e. 360 degree) contact around the nerve.

The self-wrapping overwrap configuration shown in FIGS. 14 and 15 can promote increased application speed of the lead assembly to the nerve. Prior to the lead's attachment to the vagus nerve, the lead assembly is expanded by the surgeon and aligned on the nerve. When the lead assembly is positioned correctly on the nerve, the surgeon releases the wrap, which will naturally revert to its preformed cylindrical shape, and encase or clamp onto the nerve. The shape memory of the molded material, along with the design characteristics, cause the design to return to its coiled state, which in turn secures the lead assembly to the nerve. The pressure of the collapsed structure in the rest state is adequate to gently hold the lead assembly in place. However, the surgeon can adjust the fit of the wrap to achieve the desired pressure on the nerve and apply sutures through the adjacent flanges 704, 706 to secure the wrap about the nerve to complete the implant procedure. Because of the shape memory of the overwrap material, the overwrap sheet is biased toward the substantially cylindrically wrapped configuration. However, the cylindrically wrapped shape defines a resilient encasement around the nerve which is flexible, allowing the size of the wrap to automatically conform to the size of the nerve.

By integrating the lead 710 into the self-wrapping overwrap, implantation time can be greatly reduced. It is believed that the time required to attach the nerve overwrap with integrated electrodes is comparable to the time otherwise required to attach a single helical electrode. Thus, time in the operating room and complexity of the device to be implanted are reduced. In addition, the lead assembly will have the clinical benefits of the nerve overwrap without the need for a second implanted device. Moreover, since the electrodes are integrated into the nerve overwrap, proper positioning of the electrodes with respect to the overwrap is ensured. This configuration also provides the other benefits of the nerve overwrap discussed herein, regarding current spread reduction, ease of explants, etc.

Although various embodiments have been shown and described, the invention is not so limited and will be understood to include all such modifications and variations as would be apparent to one skilled in the art. For example, equivalent elements may be substituted for those specifically shown and described, certain features may be used independently of other features, and the number and configuration of various vehicle components described above may be altered, all without departing from the spirit or scope of the invention as defined in the appended claims.

Such adaptations and modifications should and are intended to be comprehended within the meaning and range of equivalents of the disclosed exemplary embodiments. It is to be understood that the phraseology of terminology employed herein is for the purpose of description and not of limitation. Accordingly, the foregoing description of the exemplary embodiments of the invention, as set forth above, are intended to be illustrative, not limiting. Various changes, modifications, and/or adaptations may be made without departing from the spirit and scope of this invention.

What is claimed is:

1. A nerve overwrap for an implantable nerve stimulation system, the nerve overwrap comprising:
    multiple helixes including two or more electrically active helixes and an electrically inactive helix, each of the multiple helixes being configured to substantially surround a nerve of a patient in a helical configuration having more than one turn; and
    a sheet of electrically insulative material having an electrical resistivity of from about $10^8$ ohm*m to about $10^{20}$ ohm*m, wherein the sheet has dimensions configured to wrap substantially around the multiple helixes and around the nerve of the patient.

2. The nerve overwrap of claim 1, wherein:
    the two or more electrically active helixes comprise a first electrode having a first length and a second electrode having a second length; and
    the electrically inactive helix is an anchor having a third length, wherein the third length is greater than the first length and is greater than the second length.

3. The nerve overwrap of claim 1, wherein the sheet has a first thickness and a second thickness, wherein the first thickness is about 0.005 inches to 0.05 inches, wherein the second thickness is less than the first thickness, and wherein the sheet tapers from the first thickness to the second thickness.

4. The nerve overwrap of claim 1, wherein the sheet has a width that extends beyond the multiple helixes when the sheet is wrapped around the nerve of the patient.

5. The nerve overwrap of claim 1, wherein the two or more electrically active helixes comprise a first electrode and a second electrode configured to be spaced a first distance apart from each other along a length of the nerve of the patient, and wherein the sheet has a width that is at least 2.5 times greater than the first distance.

6. The nerve overwrap of claim 1, wherein the two or more electrically active helixes comprise a first electrode and a second electrode configured to be spaced a first distance apart from each other along a length of the nerve of the patient, and wherein the sheet has a width that extends beyond the first electrode and the second electrode by a distance of about 0.2 inches to 1 inch when the sheet is wrapped around the nerve of the patient.

7. The nerve overwrap of claim 1, wherein:
    when the multiple helixes are each secured around the nerve of the patient, a width of the sheet wraps around and extends beyond each of the multiple helices; and
    the sheet comprises silicone and has opposing ends that are configured to be sutured together.

8. The nerve overwrap of claim 1, further comprising a flange extending from a first end of the sheet, wherein the flange is configured to attach to a second end of the sheet when the sheet is wrapped around the nerve, wherein the second end is located at an end of the sheet that is opposite from the first end of the sheet.

9. The nerve overwrap of claim 1, wherein the two or more electrically active helixes comprise a first electrode including a first post and a second electrode including a second post, wherein the electrically inactive helix comprises a third post that does not conduct electricity, and wherein the first electrode and the second electrode are configured to be electrically connected to a pulse generation device that is configured to be implanted subcutaneously in a body of the patient.

10. The nerve overwrap of claim 9, wherein the pulse generation device is configured to wirelessly communicate with a communication device to receive information related to operation of the pulse generation device.

11. The nerve overwrap of claim 9, further comprising an electrical lead mechanically connecting each of the first post, the second post and the third post to the pulse generation device, wherein the first electrode and the second electrode are positioned on an inner surface of the sheet.

12. The nerve overwrap of claim 1, further comprising an interlocking device to connect opposing ends of the sheet together when the sheet is wrapped around the nerve, wherein the interlocking device includes an elongated tab and slot mechanism, a plurality of protrusions and slots, a strap and slot, or a combination thereof.

13. The nerve overwrap of claim 1, wherein the sheet comprises a closeable pocket, and wherein the closeable pocket is configured to surround the multiple helixes.

14. An implantable nerve stimulation system comprising:
a pulse generation device that is configured to be implanted subcutaneously in a body of a patient;
multiple helixes including two or more electrically active helixes and an electrically inactive helix, each of the multiple helixes being configured to substantially surround a nerve of the patient in a helical configuration having more than one turn, wherein the electrically active helixes are connectable to the pulse generation device; and
an overwrap including a sheet of electrically insulative material having a resistivity of from about $10^8$ ohm*m to about $10^{20}$ ohm*m, wherein the sheet has dimensions configured to wrap substantially around the multiple helixes and around the nerve of the patient.

15. The implantable nerve stimulation system of claim 14, wherein:
the two or more electrically active helixes comprise a first electrode having a first length and a second electrode having a second length; and
the electrically inactive helix is an anchor having a third length, wherein the third length is greater than the first length and is greater than the second length.

16. The implantable nerve stimulation system of claim 14, wherein the sheet has a first thickness and a second thickness, wherein the first thickness is about 0.005 inches to 0.05 inches, wherein the second thickness is less than the first thickness, and wherein the sheet tapers from the first thickness to the second thickness.

17. The implantable nerve stimulation system of claim 14, wherein the sheet has a width that extends beyond the two or more electrically active helixes by a distance of about 0.2 inches to 1 inch when the overwrap is wrapped around the nerve of the patient.

18. The implantable nerve stimulation system of claim 14, wherein the two or more electrically active helixes are configured to be spaced a first distance apart from each other along a length of the nerve of the patient, and wherein the sheet has a width that is at least two times greater than the first distance.

19. The implantable nerve stimulation system of claim 14, wherein the sheet includes a first flange at a first end of the sheet and includes a second flange at a second end of the sheet that is opposite to the first end of the sheet, and wherein the first flange and the second flange are configured to connect to each other.

20. The implantable nerve stimulation system of claim 14, wherein the sheet includes polytetrafluoroethylene (PTFE) or poly-4-hydroxybutyrate (P4HB), and wherein the pulse generation device is configured to wirelessly communicate with a communication device to receive information related to operation of the pulse generation device.

21. The implantable nerve stimulation system of claim 14, further comprising an electrical lead attached to the two or more electrically active helixes, wherein the two or more electrically active helixes are configured to be electrically connected to the pulse generation device via the electrical lead, and wherein the two or more electrically active helixes are positioned on an inner surface of the sheet.

22. The implantable nerve stimulation system of claim 14, further comprising an interlocking device to connect opposing ends of the sheet together when the overwrap is wrapped around the nerve of the patient.

23. A method for implanting a nerve stimulation system, the method comprising:
wrapping a sheet of insulative material around a nerve of a patient, wherein the insulative material has an electrical resistivity of from about $10^8$ ohm*m to about $10^{20}$ ohm*m, wherein the sheet wraps substantially around multiple helixes including two or more electrically active helixes and an electrically inactive helix and wherein, when the sheet is wrapped around the nerve, each of the multiple helixes substantially surrounds the nerve of the patient in a helical configuration having more than one turn; and
attaching opposing ends of the sheet together.

24. The nerve overwrap of claim 1, further comprising a lead connected to each of the multiple helixes, wherein two of the electrically active helixes are separated by a distance, and wherein the sheet has a width that is about 2.5 times the distance.

* * * * *